US005190961A

United States Patent [19]

Hasegawa et al.

[11] Patent Number: 5,190,961

[45] Date of Patent: Mar. 2, 1993

[54] THIOUREA DERIVATIVES AND ANTIMICROBIAL AGENT AND ANTIULCER AGENT CONTAINING THE SAME

[75] Inventors: Hirokazu Hasegawa; Isamu Endo; Shingo Koyama; Masashi Isozaki; Yukari Yoshiyama; Shigenori Nozawa; Norio Arakawa, all of Kanagawa, Japan

[73] Assignee: Terumo Kabushiki Kaisha, Tokyo, Japan

[21] Appl. No.: 739,437

[22] Filed: Aug. 2, 1991

[30] Foreign Application Priority Data

Aug. 3, 1990 [JP] Japan .................................. 2-204999
Jul. 9, 1991 [JP] Japan .................................. 3-193631

[51] Int. Cl.[5] .................... A61K 31/445; A61K 31/40; A61K 31/17; A61K 31/34; C07L 335/12; C07D 403/10; C07D 405/10; C07D 409/10

[52] U.S. Cl. ..................................... 514/331; 514/308; 514/318; 514/326; 514/343; 514/353; 514/422; 514/428; 514/438; 514/447; 514/471; 514/472; 514/586; 548/517; 548/527; 548/567; 546/193; 546/213; 546/214; 546/281; 546/231; 546/305; 546/331; 549/69; 549/77; 549/482; 549/496; 564/17; 564/22; 564/23; 564/27

[58] Field of Search ............... 546/193, 213, 214, 281, 546/231, 305, 331; 548/517, 527, 567; 549/69, 77, 482, 496; 564/17, 22, 23, 27; 514/308, 318, 326, 331, 343, 353, 422, 428, 438, 447, 471, 472, 586

[56] References Cited

U.S. PATENT DOCUMENTS 3,950,537 4/1976 De Benneville et al. ............. 564/26
4,418,209 11/1983 Douglas ................................ 564/27
4,699,915 10/1987 Cereda ................................ 548/313

OTHER PUBLICATIONS

*Chemical Abstracts*, vol. 98, Apr. 1983, Abstract No. 143,139m, Paton et al.

*Primary Examiner*—C. Warren Ivy
*Assistant Examiner*—Celia Chang
*Attorney, Agent, or Firm*—Burns, Doane, Swecker & Mathis

[57] ABSTRACT

Thiourea derivatives represented by the formula (I)

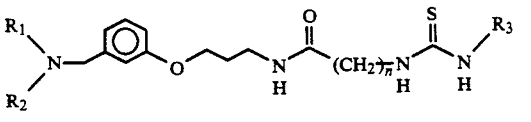

(I)

wherein $R_1$ and $R_2$ are the same or different and each represents a lower alkyl group, or $R_1$ or $R_2$ taken together represent a group having the formula $-(CH_2-)_m-$ in which m is 4 or 5, $R_3$ represents a lower alkyl group or a cycloalkyl group or a group having the formula $-(CH_2)_l-R_4$ in which $R_4$ is a phenyl, naphthyl, pyridyl, furyl or thienyl group optionally having 1-3 substituents selected from the group consisting of lower alkyl, lower alkoxy, phenoxy, lower alkylthio, hydroxy, halogen, nitro, cyano and trifluoromethyl, and l represents an integer of 0 to 2 and n represents an integer of 1 to 5 or a physiologically acceptable salt thereof.

The compounds of the invention are useful as a therapeutic agent for peptic ulcers which is also effective on prevention of the recurrence after discontinuation of the administration due to the antimicrobial activity against *Helicobacter pyroli.*

15 Claims, No Drawings

THIOUREA DERIVATIVES AND ANTIMICROBIAL AGENT AND ANTIULCER AGENT CONTAINING THE SAME

BACKGROUND OF THE INVENTION

1. Field of the Invention

This invention relates to novel thiourea derivatives and an antimicrobial agent against *Helicobacter pylori* and an antiulcer agent containing the same.

2. Description of the Prior Art

As a result of the development of histamine H2 antagonists, the therapy of peptic ulcers has become easier. However, it is now a big problem that the proportion of recurrence of the disease after discontinuing the administration of the drug is high. Since the recurrence is believed to be due to decrease in the defense factors during inhibition of the gastric secretion, it is hoped to develop a drug concurrently possessing a gastric antisecretory activity and an activity of reinforcing the defense factors. Furthermore, it has recently been found that growth of *Helicobactor pylori* occurs in a high proportion of the patients encountered with the recurrence. Consequently, attention has been drawn to the relation of the microorganism with recurrence of peptic ulcers. This suggests that a drug which has an antimicrobial activity against *Helicobacter pylori* would prevent the recurrence of peptic ulcers.

SUMMARY OF THE INVENTION

As a result of extensive studies on the synthesis and physiological action of various thiourea derivatives, we have found that the thiourea derivatives of the present invention possess not only high gastric antisecretory and defense factor-reinforcing activities but also an antimicrobial activity against *Helicobacter pylori.* The instant invention is based upon the above findings. The thiourea derivatives of the invention are useful in the therapy of peptic ulcers.

Therefore, it is an object of the invention to provide thiourea derivatives having said valuable activities.

Another object of the invention is to provide an antimicrobial agent containing said thiourea derivatives.

Further object of the invention is to provide an antiulcer agent containing said thiourea derivatives.

DETAILED DESCRIPTION OF THE INVENTION

In accordance with the present invention there are provided thiourea derivatives represented by the formula (I)

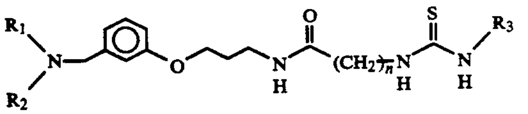
(I)

wherein $R_1$ and $R_2$ are the same or different and each represents a lower alkyl group, or $R_1$ and $R_2$ taken together represent a group having the formula $-(CH_2)_m-$ in which m is 4 or 5, $R_3$ represents a lower alkyl group or a cycloalkyl group or a group having the formula $-(CH_2)_l-R_4$ in which $R_4$ is a phenyl, naphthyl, pyridyl, furyl or thienyl group optionally having 1-3 substituents selected from the group consisting of lower alkyl, lower alkoxy, phenoxy, lower alkylthio, hydroxy, halogen, nitro, cyano and trifluoromethyl, and l represents an integer of 0 to 2 and n represents an integer of 1 to 5 or a physiologically acceptable salt thereof.

In the above definitions, lower alkyl, lower alkoxy or lower alkylthio means a group having 1-4 carbon atoms in the alkyl moiety, for example, methyl, ethyl, n-propyl, isopropyl, n-butyl, isobutyl, tert. butyl. Halogen means chlorine, bromine, iodine or fluorine, preferably chlorine.

The invention is also directed to an antimicrobial agent against *Helicobacter pylori* and an antiulcer agent containing thiourea derivatives represented by the above-mentioned formula (I) or salts thereof.

The thiourea derivatives represented by the above-mentioned formula (I) are produced by reacting an amine derivative represented by the formula (II)

(II)

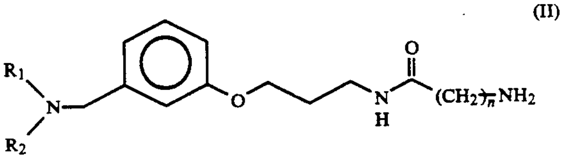

wherein $R_1$, $R_2$ and n have the same meanings as defined above with an isothiocyanate ester. As the solvent, there may be used, for example, ethanol, methanol, methylene chloride or chloroform. The reaction temperature is preferably in the range between 0° C. and a reflux temperature of a solvent used in the reaction.

$R_1$ and $R_2$ in the above-mentioned formula (I) each is a lower straight- or branched-chain alkyl group containing 1 to 4 carbon atoms, which includes, for example, methyl, ethyl, n-propyl, isopropyl, n-butyl, isobutyl and tert. butyl.

The thiourea derivatives of the invention are used as an antimicrobial agent against *Helicobacter pylori* or an antiulcer agent, dosage levels of which may be varied depending upon the symptoms and are generally 10-2000 mg, preferably 20-600 mg per day for adults. The daily dose may be divided into 1-3 doses, if required in accordance with the symptoms. The compounds of the invention can be administered in any form suitable for the administration. Oral administration is especially desirable, but intravenous injection is feasible.

The compounds of the invention as an active ingredient or one of active ingredients are formulated alone or in admixture with pharmaceutical carriers or excipients by a conventional method into various forms such as tablets, sugar-coated tablets, powders, capsules, granules, suspension, emulsion, injectable solution or the like. As examples of the carrier or excipient, there may be mentioned calcium carbonate, calcium phosphate, starch, glucose, lactose, dextrin, alginic acid, mannitol, talc, magnesium stearate and the like.

The invention will be described in more detail below with reference to examples and test examples. The examples, however, are not to be considered as the limitation of the invention.

EXAMPLES

Example 1

To a solution of N-[3-[3-(piperidinomethyl)phenoxy]-propyl]-4-(phthaloylamino)butylamide (2.00 g) in ethanol (30 ml) was added hydrazine hydrate (80%)(0.40 g). The mixture was refluxed for 2 hours. The reaction mixture was concentrated under reduced pressure followed by the addition of chloroform, stirring for a while and then filtration. The filtrate was concentrated under reduced pressure, and the residue was dissolved in ethanol (30 ml). To the solution was added methyl isothiocyanate (0.48 g), and the mixture was stirred at room temperature for 16 hours. The reaction solution was concentrated under reduced pressure, and then the residue was extracted with chloroform. The organic layer was washed with water and saturated aqueous sodium chloride, subsequently dried over anhydrous sodium sulfate and concentrated under reduced pressure. The residue was subjected to column chromatography on silica gel, and a fraction eluted with chloroform-methanol (20:1) afforded 1.09 g of 1-[3-[N-[3-[3-(piperidinomethyl)phenoxy]propyl]carbamoyl]propyl]-3-methylthiourea.

Spectroscopic data of the product support the structure of the formula (III).

NMR ($CDCl_3$) δ: 1.3-2.6 (16H, m), 3.00 (3H, d, J=4 Hz), 3.2-3.7 (6H, m), 4.00 (2H, t, J=6 Hz), 6.5-7.4 (5H, m).

(III)

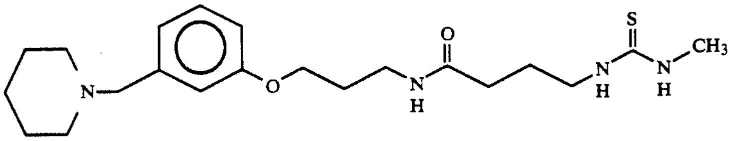

Example 2

The same procedures as in Example 1 were repeated except that n-butyl isothiocyanate was used in place of the methyl isothiocyanate used in Example 1. There was obtained 1-[3-[N- 3- 3-(piperidinomethyl)phenoxy]propyl]carbamoyl]propyl]-3-n-butylthiourea. Spectrometric data of the product support the structure of the formula (IV).

NMR ($CDCl_3$) δ: 0.6-2.6 (25H, m), 3.2-3.8 (6H, m), 4.03 (2H, t, J=6 Hz), 6.3-7.4 (m, 5H).

(IV)

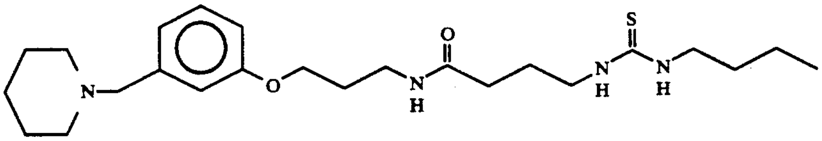

Example 3

The same procedures as in Example 1 were repeated except that phenyl isothiocyanate was used in place of the methyl isothiocyanate used in Example 1. There was obtained 1-[3-[N-(3-[3-(piperidinomethyl)phenoxy]propyl]carbamoyl]propyl]-3-phenylthiourea. Spectrometric data of the product support the structure of the formula (V).

NMR ($CDCl_3$) δ: 1.3-2.6 (16H, m), 3.2-3.8 (6H, m), 4.00 (2H, t, J=6 Hz), 6.3-7.5 (m, 10H).

(V)

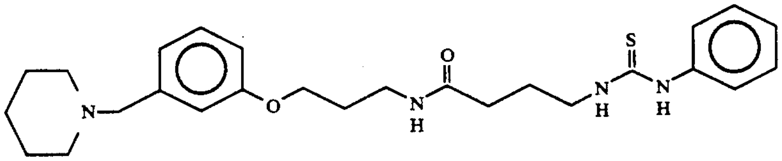

Example 4

The same procedures as in Example 1 were repeated except that p-chlorophenyl isothiocyanate was used in place of the methyl isothiocyanate used in Example 1. There was obtained 1-[3-[N-[3-[3-(piperidinomethyl)phenoxy]propyl]carbamoyl]propyl]-3-(p-chlorophenyl)thiourea. Spectrometric data of the product support the structure of the formula (VI).

NMR ($CDCl_3$) δ: 1.3-2.6 (16H, m), 3.2-3.8 (6H, m), 4.02 (2H, t, J=6 Hz), 6.5-7.5 (m, 9H).

(VI)

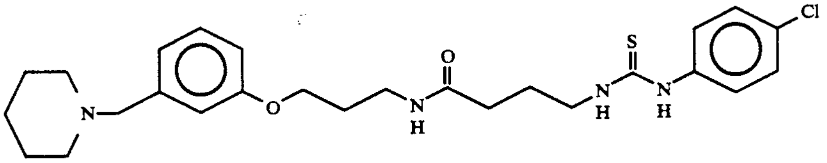

Example 5

The same procedures as in Example 1 were repeated except that cyclohexyl isothiocyanate was used in place of the methyl isothiocyanate used in Example 1. There was obtained 1-[3-[N-[3-[3-(piperidinomethyl)phenoxy]propyl]carbamoyl]propyl]-3-cyclohexylthiourea. Spectrometric data of the product support the structure of the formula (VII).

NMR ($CDCl_3$) δ: 1.0-2.6 (27H, m), 3.2-3.8 (6H, m), 4.05 (2H, t, J=6 Hz), 6.8-7.5 (5H, m).

(VII)

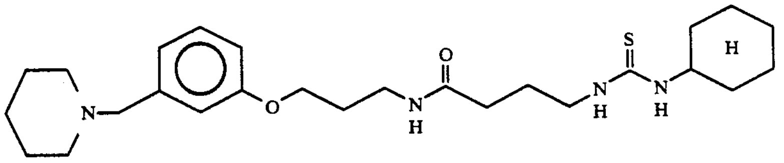

Example 6

The same procedures as in Example 1 were repeated except that β-phenethyl isothiocyanate was used in place of the methyl isothiocyanate used in Example 1. There was obtained 1- 3-[N- 3- 3-(piperidinomethyl)-phenoxy]carbamoyl]propyl]-3-(8-phenethyl)thiourea. Spectrometric data of the product support the structure of the formula (VIII).

NMR ($CDCl_3$) δ: 1.3–2.6 (16H, m), 2.7–3.8 (10H, m), 4.00 (2H, t, J=6 Hz), 6.5–7.4 (10H, m).

Example 8

The same procedures as in Example 1 were repeated except that 3-pyridyl isothiocyanate was used in place of the methyl isothiocyanate used in Example 1. There was obtained 1-[3-[N-[3- 3-(piperidinomethyl)phenoxy)-propyl]carbamoyl]propyl]-3-(3-pyridyl)thiourea. Spectrometric data of the product support the structure of the formula (X).

NMR ($CDCl_3$) δ: 1.3–2.6 (16H, m), 3.2–3.8 (6H, m), 4.00 (2H, t, J=6 Hz), 6.7–8.7 (9H, m).

(VIII)

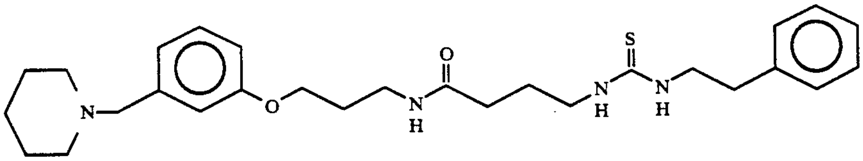

(X)

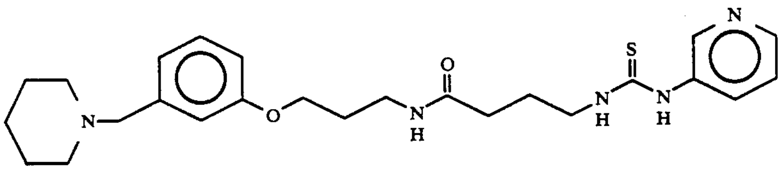

Example 7

The same procedures as in Example 1 were repeated except that 1-naphthyl isothiocyanate was used in place of the methyl isothiocyanate used in Example 1. There was obtained 1-[3-[N-[3-[3-(piperidinomethyl)phenoxy]-propyl]carbamoyl]propyl]-3-(1-naphthyl)thiourea. Spectrometric data of the product support the structure of the formula (IX).

NMR ($CDCl_3$) δ: 1.3–2.6 (16H, m), 3.2–3.8 (6H, m), 4.00 (2H, t, J=6 Hz), 6.3–7.6 (12H, m).

Example 9

The same procedures as in Example 1 were repeated except that N-[3-[3-(pyrrolidinomethyl)phenoxy]-propyl]-4-(phthaloylamino)butylamide was used in place of N-[3-[3-(piperidinomethyl)phenoxy]propyl]-4-(phthaloylamino)butylamide and phenyl isothiocyanate was used in place of the methyl isothiocyanate used in Example 1. There was obtained 1-[3-[N-[3-[3-(pyrrolidinomethyl)phenoxy]propyl]carbamoyl]propyl]-3-phenylthiourea. Spectrometric data of the product support the structure of the formula (XI).

NMR ($CDCl_3$) δ: 1.4–2.7 (14H, m), 3.1–3.8 (6H, m), 4.00 (2H, t, J=6 Hz), 6.5–7.4 (10H, m).

(IX)

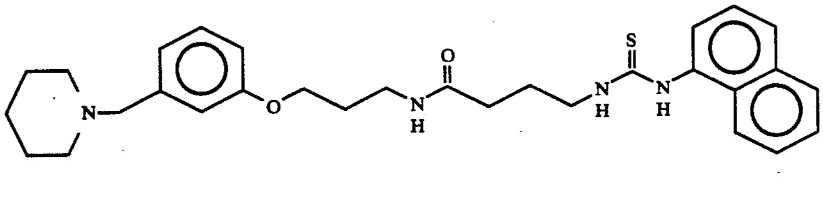

(XI)

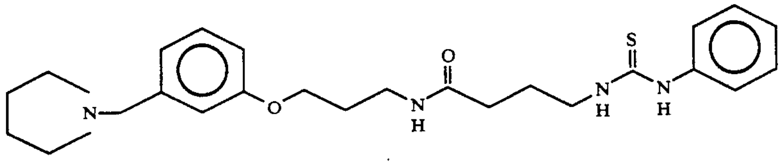

Example 10

The same procedures as in Example 1 were repeated except that O-methylphenyl isothiocyanate was used in place of the methyl isothiocyanate used in Example 1. There was obtained 1-[3-[N-[3-[3-(piperidinomethyl)-phenoxyl]propyl]carbamoyl]propyl]-3-(O-methyl-phenyl)thiourea. Spectrometric data of the product support the structure of the formula (XII).

NMR ($CDCl_3$) δ: 1.3–2.6 (16H, m), 2.3 (3H, s), 3.2–3.8 (6H, m), 4.00 (2H, t, J=6 Hz), 6.3–7.4 (10H, m), 8.2 (1H, bs).

Example 12

The same procedure as in Example 1 were repeated except that 2,4,6-trimethylphenyl isothiocyanate was used in place of the methyl isothiocyanate used in Example 1. There was obtained 1-[3-[N-[3-[3-(piperidinomethyl)phenoxy]propyl]carbamoyl]propyl]-3-(2,4,6-trimethylphenyl)thiourea. Spectrometric data of the product support the structure of the formula (XIV).

NMR ($CDCl_3$) δ: 1.4–2.6 (25H, m), 3.2–3.8 (6H, m), 4.0 (2H, t, J=6 Hz), 6.3–7.8 (9H, m).

(XII)

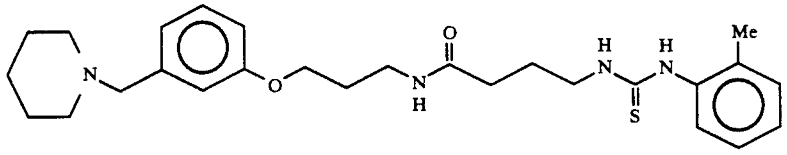

(XIV)

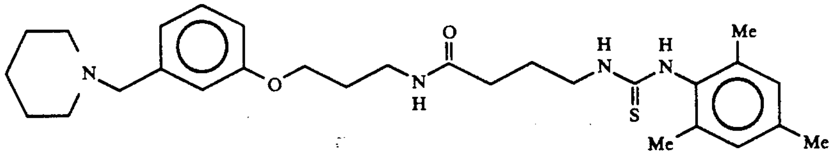

Example 11

The same procedures as in Example 1were repeated except that 3,5-dimethylphenyl isothiocyanate was used in place of the methyl isothiocyanate used in Example 1. There was obtained 1-[3-[N-[3-[3-(piperidinomethyl)-phenoxy]propyl]carbamoyl]propyl]-3-(3,5-dimethyl-phenyl)thiourea.

NMR ($CDCl_3$) δ: 1.3–2.6 (16H, m), 2.35 (6H, S), 3.2–3.8 (6H, m), 4.00 (2H, t, J=6 Hz), 6.3–7.4 (9H, m), 8.21 (1H, bs).

Example 13

The same procedures as in Example 1 were repeated except that p-isopropylphenyl isothiocyanate was used in place of the methyl isothiocyanate used in Example 1. There was obtained 1-[3-[N-[3-[3-(piperidinomethyl)-phenoxy]propyl]carbamoyl]propyl]-3-(p-isopropyl-phenyl)thiourea. Spectrometric data of the product support the structure of the formula (XV).

NMR ($CDCl_3$) δ: 1.23 (6H, d, J=7 Hz), 1.3–2.6 (16H, m), 2.7–3.0 (1H, m), 3.1–3.8 (6H, m), 4.00 (2H, t, J=6 Hz), 6.2–7.4 (10H, m), 8.37 (1H, bs).

(XIII)

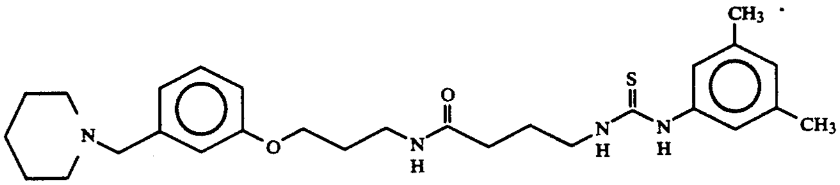

(XV)

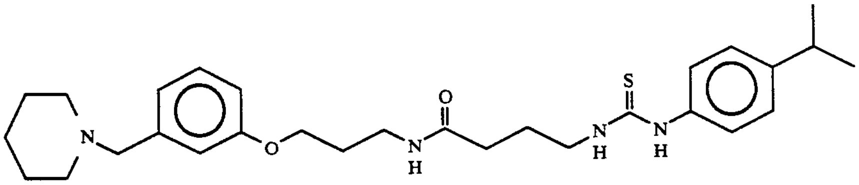

Example 14

The same procedure as in Example 1 were repeated except that O-methoxyphenyl isothiocyanate was used in place of the methyl isothiocyanate used in Example 1. There was obtained 1-[3-[N-[3-[3-(piperidinomethyl)-phenoxy]propyl]-carbamoyl]propyl]-3-(O-methoxy-phenyl)thiourea. Spectrometric data of the product support the structure of the formula (XVI).

NMR ($CDCl_3$) δ: 1.3–2.5 (16H, m), 3.2–3.9 (9H, m), 4.00 (2H, t, J=6 Hz), 6.1–7.7 (11H, m).

Example 16

The same procedure as in Example 1 were repeated except that O-n-butoxyphenyl isothiocyanate was used in place of the methyl isothiocyanate used in Example 1. There was obtained 1-[3-[N-[3-[3-(piperidinomethyl)-phenoxy]propyl]carbamoyl]propyl]-3-(O-n-buthoxy-phenyl)thiourea. Spectrometric data of the product support the structure of the formula (XVIII).

NMR ($CDCl_3$) δ: 0.97 (3H, bt), 1.3–2.7 (20H, m), 3.1–3.8 (4H, m), 3.43 (s, 2H), 3.94 (2H, t, J=6 Hz), 4.00 (2H, t, J=6 Hz), 6.1–7.4 (10H, m), 8.04 (1H, bs).

(XVI)

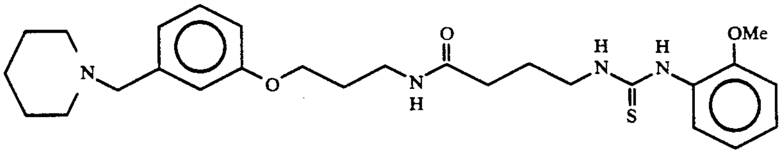

(XVIII)

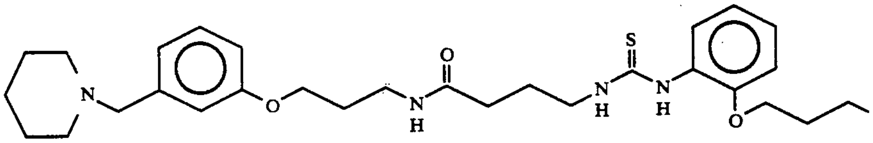

Example 15

The same procedures as in Example 1 were repeated except that 3-methoxyphenyl isothiocyanate was used in place of the methyl isothiocyanate used in Example 1. There was obtained 1-[3-[N-[3-[3-(piperidinomethyl)-phenoxy]propyl]carbamoyl]propyl]-3-(3-methoxy-phenyl)thiourea. Spectrometric data of the product support the structure of the formula (XVII).

NMR ($CDCl_3$) δ: 1.1–2.6 (16H, m), 3.1–3.7 (6H, m), 3.77 (3H, s), 3.98 (2H, t, J=6 Hz), 6.3 (1H, bs), 6.6–7.4 (8H, m), 8.21 (1H, bs).

Example 17

The same procedure as in Example 1 were repeated except that O-phenoxyphenyl isothiocyanate was used in place of the methyl isothiocyanate used in Example 1. There was obtained 1-[3-[N-[3-[3-(piperidinomethyl)-phenoxy]propyl]carbamoyl]propyl]-3-(O-phenoxy-phenyl)thiourea. Spectrometric data of the product support the structure of the formula (XIX).

NMR ($CDCl_3$) δ: 1.3–2.7 (16H, m), 3.1–4.3 (8H, m), 6.4–7.9 (15H, m), 8.2 (1H, bs).

(XVII)

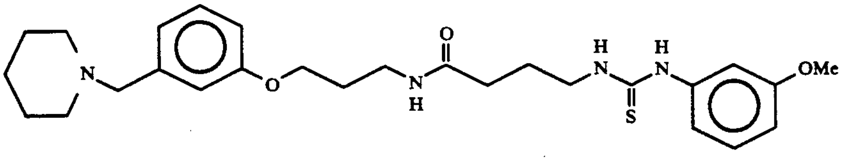

(XIX)

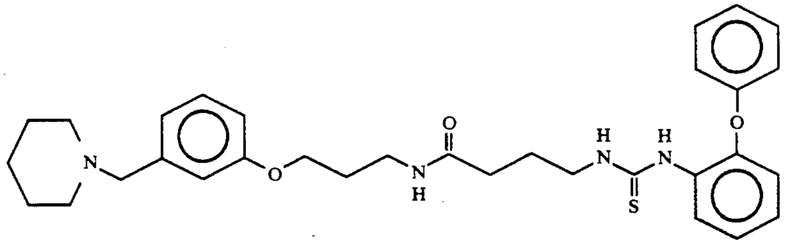

Example 18

The same procedure as in Example 1 were repeated except that 3,4,5-trimethoxyphenyl isothiocyanate was used in place of the methyl isothiocyanate used in Example 1. There was obtained 1-[3-[N-[3-[3-(piperidinomethyl)phenoxy]propyl]carbamoyl]propyl]-3-(3,4,5-trimethoxyphenyl)thiourea. Spectrometric data of the product support the structure of the formula (XX).

NMR ($CDCl_3$) δ: 1.3–2.6 (16H, m), 3.2–4.3 (6H, m), 3.42 ) 2H, s), 3.80 (9H, s), 6.3–7.3 (8H, m), 8.60 (1H, bs).

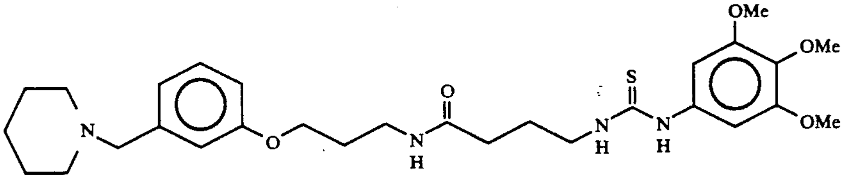

(XX)

The same procedure as in Example 1 were repeated except that 2-methoxy-6-methylphenyl isothiocyanate was used in place of the methyl isothiocyanate used in Example 1. There was obtained 1-[3-[N-[3-[3-(piperidinomethyl)phenoxy]propyl]carbamoyl]propyl]-3-(2-methoxy-6-methylphenyl)thiourea. Spectrometric data of the product support the structure of the formula (XXI).

NMR ($CDCl_3$) δ: 1.3–2.6 (16H, m), 2.24 (3H, s), 3.1–4.2 (6H, m), 3.43 (2H, s), 3.77 (3H, s), 5.9–7.4 (10H, m).

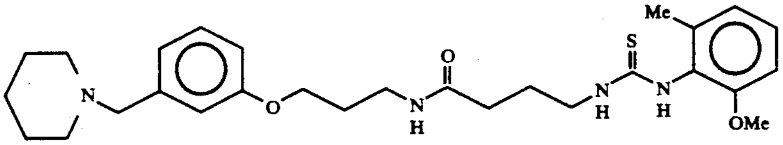

(XXI)

Example 20

The same procedure as in Example 1 were repeated except that 3-cyanophenyl isothiocyanate was used in place of the methyl isothiocyanate used in Example 1. There was obtained 1-[3-[N-[3-[3-(piperidinomethyl)-phenoxy]propyl]carbamoyl]propyl]-3-(3-cyanophenyl)-thiourea. Spectrometric data of the product support the structure of the formula (XXII).

NMR ($CDCl_3$) δ: 1.3–2.6 (16H, m), 3.2–3.8 (6H, m), 4.00 (2H, t, J=6 Hz), 6.2 7.4 (11H, m).

(XXII)

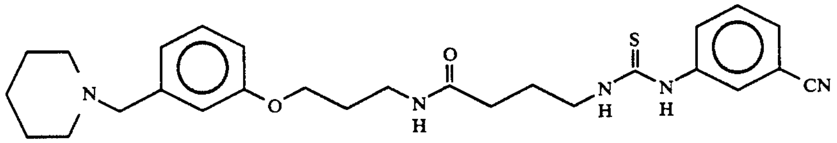

Example 21

The same procedure as in Example 1 were repeated except that 2-methylthiophenyl isothiocyanate was used in place of the methyl isothiocyanate used in Example 1. There was obtained 1-[3-[N-[3-[3-(piperidinomethyl)-phenoxy]propyl]carbamoyl]propyl]-3-(2-methylthio-phenyl)thiourea. Spectrometric data of the product support the structure of the formula (XXIII).

NMR ($CDCl_3$) δ: 1.3–2.6 (16H, m), 2.33 (3H, m), 3.2–3.8 (4H, m), 3.43 (2H, s), 4.00 (2H, t, J=6 Hz), 6.0–7.4 (10H, m), 7.83 (1H, bs).

(XXIII)

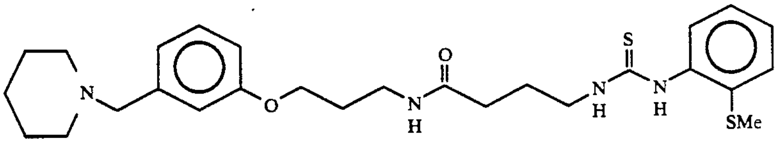

Example 22

The same procedure as in Example 1 were repeated except that 2-trifluoromethylphenyl isothiocyanate was used in place of the methyl isothiocyanate used in Example 1. There was obtained 1-[3-[N-[3-[3-(piperidinomethyl)phenoxy]propyl]carbamoyl]propyl]-3-(2-trifluoromethylphenyl)thiourea. Spectrometric data of the product support the structure of the formula (XXIV).

NMR ($CDCl_3$) δ: 1.3–2.6 (16H, m), 3.2–3.8 (4H, m), 3.43 (2H, s), 4.00 (2H, t, J=6 Hz), 6.3–7.8 (11H, m).

(XXIV)

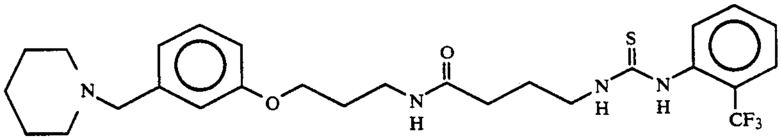

Example 23

The same procedure as in Example 1 were repeated except that O-nitrophenyl isothiocyanate was used in place of the methyl isothiocyanate used in Example 1. There was obtained 1-[3-[N-[3-[3-(piperidinomethyl)-phenoxy]propyl]carbamoyl]propyl]-3-(O-nitrophenyl)-thiourea. Spectrometric data of the product support the structure of the formula (XXV).

NMR ($CDCl_3$) δ: 1.2–2.7 (16H, m), 3.2–4.1 (8H, m), 6.4–8.8 (11H, m).

(XXV)

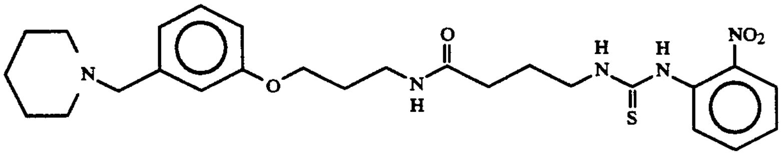

Example 24

The same procedure as in Example 1 were repeated except that 2-methoxymethoxyphenyl isothiocyanate was used in place of the methyl isothiocyanate used in Example 1. There was obtained 1-[3-[N-[3-[3-(piperidinomethyl)phenoxy]propyl]carbamoyl]propyl]-3-(2-methoxymethoxyphenyl)thiourea. Spectrometric data of the product support the structure of the formula (XXVI).

NMR ($CDCl_3$) δ: 1.3–2.6 (16H, m), 3.2–3.8 (4H, m), 3.44 (2H, s), 4.00 (2H, t, J=6 Hz), 6.2–7.7 (10H, m), 7.80 (1H, bs).

(XXVI)

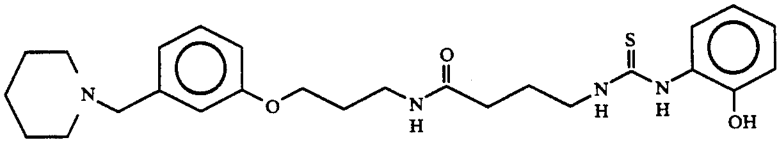

Example 25

The same procedure as in Example 1 were repeated except that 3-(6-methoxypyridyl) isothiocyanate was used in place of the methyl isothiocyanate used in Example 1. There was obtained 1-[3-[N-[3-[3-(piperidinomethyl)phenoxy]propyl]carbamoyl]propyl]-3-[3-(6-methoxypyridyl)]thiourea. Spectrometric data of the product support the structure of the formula (XXVII).

NMR ($CDCl_3$) δ: 1.3–2.6 (16H, m), 3.1–3.9 (4H, m), 3.43 (2H, s), 3.90 (3H, s), 4.00 (2H, t, J=6 Hz), 6.4–7.8 (8H, m), 8.07 (1H, d, J=2 Hz), 8.57 (1Hbs).

(XXVII)

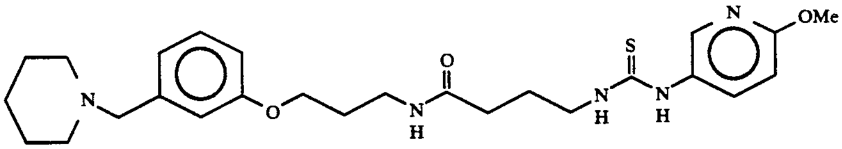

Example 26

The same procedures as in Example 1 were repeated except that furfuryl isothiocyanate was used in place of the methyl isothiocyanate used in Example 1. There was obtained 1-[3-[N-[3-[3-(piperidinomethyl)phenoxy]propyl]carbamoyl]propyl]-3-furfurylthiourea. Spectrometric data of the product support the structure of the formula (XXVIII).

NMR ($CDCl_3$) δ: 1.2–2.5 (16H, m), 3.1–3.7 (6H, m), 3.9 (2H, t, J=6 Hz), 4.7 (2H, d, J=7 Hz), 6.1–7.3 (10H, m).

lesions developed in the glandular stomach area was then measured. Results were expressed in sum of the lesions per animal which was referred to as peptic ulcer index. The results are shown in Table 1.

As apparent from the table, the compounds of the invention were found to have a high antiulcer activity. It was confirmed that the thiourea derivatives of the invention not shown in the table also have a similar antiulcer activity.

(XXVIII)

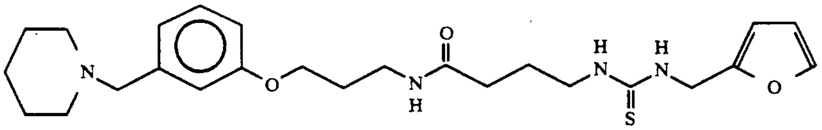

Example 27

The same procedures as in Example 1 were repeated except that 2-thienylmethyl isothiocyanate was used in place of the methyl isothiocyanate used in Example 1. There was obtained 1-[3-[N-[3-[3-(piperidinomethyl)-phenoxy]propyl]carbamoyl]propyl]-3-(2-thienylmethyl)thiourea. Spectrometric data of the product support the structure of the formula (XXIX).

NMR ($CDCl_3$) δ: 1.2–2.7 (16H, m), 3.2–3.7 (6H, m), 4.0 (2H, t, J=6 Hz), 4.9 (2H, d, J=6 Hz), 6.5–7.5 (9H, m).

Percent inhibition of the peptic ulcer formation (%) as shown in the table was calculated according to the following equation:

$$\left(1-\frac{\text{Ulcer index for rats orally receiving a thiourea derivative of the invention}}{\text{Ulcer index for rats not receiving a thiourea derivative of the invention}}\right)\times 100$$

(XXIX)

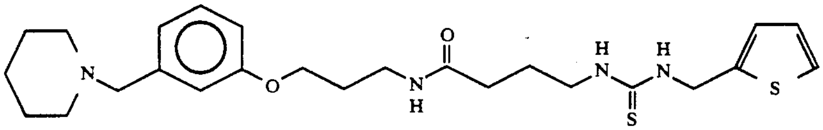

Example 28

The same procedures as in Example 1 were repeated except that phenyl isothiocyanate was used in place of the methyl isothiocyanate and N-[3-[3-(piperidinomethyl)phenoxy]propyl]-6-(phthaloylamino) was used in place of N-[3-[3-(piperidinomethyl)phenoxy]propyl]-4-(phthaloylamino)butylamide in Example 1. There was obtained 1-[5-[N-[3-[3-(piperidinomethyl)phenoxy]-propyl]carbamoyl]pentyl]-3-phenylthiourea. Spectrometric data of the product support the structure of the formula (XXX).

NMR ($CDCl_3$) δ: 1.2–2.6 (20H, m), 3.2–3.8 (6H, m), 4.00 (2H, t, J=6 Hz), 6.3–7.4 (10H, m), 8.25 (1H, bs).

(2) Inhibitory action against ethanol peptic ulcer

SD male rats (weighing 200–300 g) were fasted for 24 hours before oral administration of a thiourea derivative of the invention at a dose of 32 mg/kg bodyweight. One hour later, ethanol was orally given in a volume of 0.5 ml/100 g bodyweight. One hour after treating with ethanol, the rat was sacrificed with ether, and the stomach was excised and treated with formalin. Area ($mm^2$) of the lesions developed in the glandular stomach area was then measured. Results were expressed in sum of the lesions per animal which was referred to as peptic ulcer index. The results are shown in Table 1.

As apparent from the table, the compounds of the invention were found to have a high antiulcer activity. It was confirmed that the thiourea derivatives of the invention not shown in the table also have a similar antiulcer activity.

(XXX)

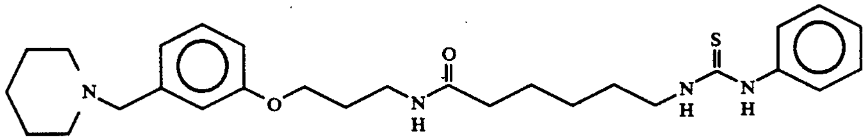

Test Example (1) Inhibitory action against the peptic ulcer induced by water immersion restraint stress SD male rats (weighing 200–300 g) were fasted for 24 hours before oral administration of a thiourea derivative of the invention at a dose of 32 mg/kg bodyweight. One hour later, the animal was put in a stress cage and loaded with water immersion restraint stress in a water bath at 23° C. Seven hours after loading with the stress, the rate was sacrificed with ether, and the stomach was excised and treated with formalin. Area ($mm^2$) of the Percent inhibition of the peptic ulcer formation (%) as shown in the table was calculated according to the same equation as mentioned above.

(3) Antimicrobial activity against *Helicobacter pylori*

Antimicrobial activity of the thiourea derivatives according to the invention against *Helicobacter pylori*

(or *Campylobacter pylori*) was evaluated by employing strain NCTC 11916 as a Helicobacter test organism and determining MIC (minimum inhibitory concentration) for the strain with the thiourea derivative.

The *Helicobacter pylori* was pre-incubated in a plate medium for 3-5 days. The medium was prepared by dissolving 38 g of a Mueller-Hinton medium (manufactured by Difco) in an appropriate amount of distilled water, sterilizing the solution in an autoclave, adding to the solution 50 ml of a horse hemolysis solution (manufactured by Nippon Seibutu Zairyou Center: Horse defibrinized blood, hemolyzed by a lyophilization treatment) and 2 ml of Skirrow, a Campylobacter selective supplement (manufactured by OXOID) containing vancomycin (5 mg), trimethoprim (2.5 mg) and polymyxin B (1250 IU) per vial (2 ml), and further an appropriate amount of distilled water to a volume of 1L in total and expanding and solidifying the solution on a dish. These antibiotics were contained for inhibition of the growth of microorganism other than *Helicobacter pylori*. The *Helicobacter pylori* pre-incubated under slightly aerobic conditions (an $O_2$ concentration of about 5%) at 37° C. for 3-5 days was suspended in a physiological saline solution in a concentration of approximately $10^8$ organisms/ml. Approximately 10-20 μl of the suspension was inoculated on a medium for MIC measurement in cross streaks. The medium for MIC measurement was prepared by mixing a solution of the same composition as that of the medium for pre-incubation and a solution of a thiourea derivative according to the invention in DMSO (dimethylsulfoxide; a final concentration of 2.5% or below) at a ratio of 9:1 and solidifying the mixture on a dish. The DMSO solution was formed by the twofold dilution method. As in the pre-incubation, the *Helicobacter pylori* was cultured under slightly aerobic conditions at 37° C. for 3-5 days. After completion of the culture, growth of the microoranisms on the streaks was visually determined. The minimum concentration of the thiourea derivative in which no growth was observed was taken as MIC. The results are shown in Table 1.

As apparent from Table 1, the compounds of the invention were found to possess a marked antimicrobial activity. It was confirmed that the thiourea derivatives of the invention not shown in the table also have a similar antimicrobial activity.

TABLE 1

Pharmacological profiles of the thiourea derivative

| Example No. | Inhibitory action against stress peptic ulcer Percent inhibition of p.u.* formation (%) | Inhibitory action against ethanol peptic ulcer Percent inhibition of p.u.* formation (%) | Antimicrobial activity against *Helicobacter pylori* MIC (μg/ml) |
|---|---|---|---|
| 1 | 92.1 | 51.4 | 6.25 |
| 2 | 67.1 | 75.7 | 6.25 |
| 3 | 80.5 | 88.7 | 12.5 |
| 4 | 74.6 | 78.2 | 6.25 |
| 5 | 70.5 | 82.3 | 6.25 |
| 6 | 76.9 | 84.4 | 6.25 |
| 7 | 88.3 | 92.0 | 6.25 |
| 8 | 82.2 | 65.0 | 12.5 |
| 9 | 58.6 | 77.9 | 6.25 |
| 10 | 82.2 | 94.2 | 6.25 |
| 11 | 85.5 | 92.8 | 6.25 |
| 12 | 77.1 | 80.2 | 6.25 |
| 13 | 77.3 | 90.2 | 6.25 |
| 14 | 91.2 | 94.3 | 6.25 |
| 15 | 78.3 | 92.1 | 6.25 |
| 16 | 71.7 | 93.3 | 6.25 |
| 17 | 62.2 | 73.3 | 12.5 |

TABLE 1-continued

Pharmacological profiles of the thiourea derivative

| Example No. | Inhibitory action against stress peptic ulcer Percent inhibition of p.u.* formation (%) | Inhibitory action against ethanol peptic ulcer Percent inhibition of p.u.* formation (%) | Antimicrobial activity against *Helicobacter pylori* MIC (μg/ml) |
|---|---|---|---|
| 18 | 60.6 | 83.8 | 6.25 |
| 19 | 90.1 | 94.6 | 6.25 |
| 20 | 70.2 | 83.5 | 12.5 |
| 21 | 85.5 | 81.1 | 6.25 |
| 22 | 83.3 | 76.4 | 6.25 |
| 23 | 76.4 | 72.3 | 6.25 |
| 24 | 60.3 | 70.3 | 12.5 |
| 25 | 65.6 | 72.5 | 6.25 |
| 26 | 74.4 | 90.3 | 6.25 |
| 27 | 72.5 | 88.2 | 6.25 |
| 28 | 73.2 | 75.5 | 12.5 |

*peptic ulcer

Acute toxicity

An acute toxicity test was carried out with ICR male mice (5 weeks old) by oral administration. $LD_{50}$ was 1000 mg/kg or higher with any of the compounds of the invention thereby demonstrating high safety as compared with the effective dose.

According to the present invention, there are provided novel thiourea derivatives and an antimicrobial agent and an antipeptic ulcer agent containing the same. It was demonstrated that the above-mentioned compounds of the invention possess high antiulcer activities. Thus, they can effectively be used as a therapeutic agent for peptic ulcers since they promote cure of the peptic ulcers by inhibition of gastric secretion, and additionally, they can prevent the recurrence after discontinuation of the administration due to their strong defense factor-reinforcing activity as well as their antimicrobial activity against *Helicobacter pylori*.

What is claimed is:

1. A thiourea compound represented by the formula (I)

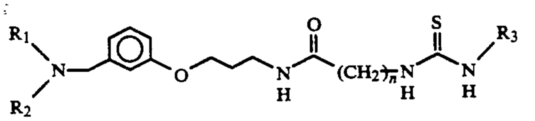

(I)

wherein $R_1$ and $R_2$ are the same or different and each represents a lower alkyl group, or $R_1$ and $R_2$ taken together represent a group having the formula $-(CH_2)_m-$ in which m is 4 or 5, $R_3$ represents a lower alkyl group or a cycloalkyl group or a group having the formula $-(CH_2)_l-R_4$ in which $R_4$ is a phenyl, naphthyl, pyridyl, furyl or thienyl group optionally having 1-3 substituents selected from the group consisting of lower alkyl, lower alkoxy, phenoxy, lower alkylthio, hydroxy, halogen, nitro, cyano and trifluoromethyl, and l represents an integer of 0 to 2 and n represents an integer of 1 to 5 or a physiologically acceptable salt thereof.

2. The thiourea compound according to claim 1, wherein $R_3$ represents a group having the formula $-(CH_2)_l-R_4$ in which l is an integer of 0 and $R_4$ is a phenyl, naphthyl or pyridyl group optionally having 1-3 substituents selected from the group consisting of lower alkyl, lower alkoxy, phenoxy, lower alkylthio, hydroxy, halogen, nitro, cyano and trifluoromethyl.

3. The thiourea compound according to claim 1, wherein $R_3$ represents a group having the formula $-(CH_2)_l-R_4$ in which l is an integer of 1 and $R_4$ is a furyl or thienyl group.

4. An antimicrobial agent against *Helicobacter pylori* comprising an antimicrobially effective amount of the thiourea compound or physiologically acceptable salt thereof according to claim 1 in combination with a pharmaceutically acceptable carrier or excipient.

5. An antiulcer agent comprising an antiulcer effective amount of the thiourea compound or physiologically acceptable salt thereof according to claim 1 in combination with a pharmaceutically acceptable carrier or excipient.

6. An antimicrobial agent against *Helicobacter pylori* comprising an antimicrobially effective amount of the thiourea compound or physiologically acceptable salt thereof according to claim 2 in combination with a pharmaceutically acceptable carrier or excipient.

7. An antimicrobial agent against *Helicobacter pylori* comprising an antimicrobially effective amount of the thiourea compound or physiologically acceptable salt thereof according to claim 3 in combination with a pharmaceutically acceptable carrier or excipient.

8. An antiulcer agent comprising an antiulcer effective amount of the thiourea compound or physiologically acceptable salt thereof according to claim 1 in combination with a pharmaceutically acceptable carrier or excipient.

9. An antiulcer agent comprising an antiulcer effective amount of the thiourea compound or physiologically acceptable salt thereof according to claim 3 in combination with a pharmaceutically acceptable carrier or excipient.

10. A method for treating *Helicobacter pylori* infection in a *Helicobacter pylori* infected subject comprising administration of an antimicrobially effective amount of the thiourea compound or physiologically acceptable salt thereof according to claim 1.

11. A method for treating *Helicobacter pylori* infection in a *Helicobacter pylori* infected subject comprising administration of an antimicrobially effective amount of the thiourea compound or physiologically acceptable salt thereof according to claim 2.

12. A method for treating *Helicobacter pylori* infection in a *Helicobacter pylori* infected subject comprising administration of an antimicrobially effective amount of the thiourea compound or physiologically acceptable salt thereof according to claim 3.

13. A method for treating ulcers comprising administering to a subject suffering from an ulcer an antiulcer effective amount of the thiourea compound or physiologically acceptable salt thereof to claim 1.

14. A method for treating ulcers comprising administering to a subject suffering from an ulcer an antiulcer effective amount of the thiourea compound or physiologically acceptable salt thereof to claim 2.

15. A method for treating ulcers comprising administering to a subject suffering from an ulcer an antiulcer effective amount of the thiourea compound or physiologically acceptable salt thereof to claim 3.

* * * * *

UNITED STATES PATENT AND TRADEMARK OFFICE

CERTIFICATE OF CORRECTION

PATENT NO. : 5,190,961 Page 1 of 2

DATED : March 2, 1993

INVENTOR(S) : Hirokazu HASEGAWA ET AL

It is certified that error appears in the above-identified patent and that said Letters Patent is hereby corrected as shown below:

In Column 5, line 17, delete "phenoxy]carbamoyl]propyl]-3-(8-phenethyl)-thiourea" and insert -- phenoxy]propyl]carbamoyl]propyl] -3-(. phenethyl)thiourea --.

In Column 7, line 53, after "phenyl)thiourea.", insert -- Spectrometric data of the product support the structure of the formula (XIII). --.

In Column 8, line 13, delete "procedure" and insert -- procedures --.

In Column 9, line 14, delete "procedure" and insert -- procedures --.

In Column 10, line 14, delete "procedure" and insert -- procedures --.

In Column 10, line 49, delete "procedure" and insert -- procedures --.

In Column 11, line 16, delete "procedure" and insert -- procedures --.

In Column 11, line 35, delete ")2H, s)" and insert -- (2H, s) --.
line 48, insert heading --Example 1a--.

In Column 11, line 49, delete "procedure" and insert -- procedures --.

In Column 12, line 16, delete "procedure" and insert -- procedures --.

In Column 12, line 49, delete "procedure" and insert -- procedures --.

In Column 12, line 56, delete "(3H, m)" and insert -- (3H, s) --.

In Column 13, line 11, delete "procedure" and insert -- procedures --.

In Column 13, line 38, delete "procedure" and insert -- procedures --.

UNITED STATES PATENT AND TRADEMARK OFFICE
CERTIFICATE OF CORRECTION

PATENT NO. : 5,190,961

DATED : March 2, 1993

INVENTOR(S) : Hirokazu HASEGAWA et al

It is certified that error appears in the above-identified patent and that said Letters Patent is hereby corrected as shown below:

In Column 13, line 66, delete "procedure" and insert -- procedures --.

In Column 16, line 21, insert -- Percent inhibition of the peptic ulcer formation (%) = --.

In Column 17, line 20, delete "microorganism" and insert -- microorganisms --.

In Column 19, line 27, delete "1" and insert -- 2 --.

Signed and Sealed this

Fourth Day of January, 1994

Attest:

BRUCE LEHMAN

*Attesting Officer*

*Commissioner of Patents and Trademarks*